United States Patent [19]

Swim et al.

[11] Plant 4,243

[45] Apr. 25, 1978

[54] ROSE PLANT

[75] Inventors: Herbert C. Swim, Ontario; Arnold W. Ellis, Bakersfield, both of Calif.

[73] Assignee: Armstrong Nurseries, Inc., Ontario, Calif.

[21] Appl. No.: 787,285

[22] Filed: Apr. 13, 1977

[51] Int. Cl.[2] ..... A01H 5/02

[52] U.S. Cl. ..... Plt./11

[58] Field of Search ..... Plt./11

*Primary Examiner*—Robert E. Bagwill
*Assistant Examiner*—James R. Feyrer
*Attorney, Agent, or Firm*—Andrew R. Klein

[57] ABSTRACT

A new hybrid tea rose of the tall bush type, tender to semihardy, raised as an outdoor seedling and useful primarily for garden decoration. The most notable characteristic is the bicolor nature of the blooms which have a general color effect between orange and yellow, usually with 25 to 35 petals plus 1–5 petaloids, and a color reverse, especially on the outer petals. The color changes from reddish orange to yellowish pink as the flower matures.

1 Drawing Figure

This invention relates to a new variety of hybrid tea rose of the tall bush outdoor type. It is from tender to semihardy and is raised as a seedling for garden decoration. The rose described herein was grown in Ontario, Calif., and the observations made generally relate to that climatic zone.

The seed parent of this new variety was "Arlene Francis" (U.S. Plant Pat. No. 1,684), and the pollen parent was "Bewitched" (U.S. Plant Pat. No. 2,755).

The new variety may be distinguished from its seed parent most notably by its bicolor flowers. Whereas the seed parent has flowers of a relatively uniform golden yellow coloration, the new variety is from orange to orange-pink in color, with a yellow reverse to the petals. Furthermore, the new variety has a wider range of petals than "Arlene Francis", for it may have from 25 to 35 petals, plus 1 to 5 petaloids, as compared to "Arlene Francis", which has from 25 to 30 petals. It may also be noted that the stamen filaments of the new cultivar are predominantly yellow, as compared to the stamen filaments of "Arlene Francis", which are predominantly red.

The new variety differs most notably from its pollen parent likewise in respect of flower color. Whereas "Bewitched" is relatively uniformly pink, or more precisely, rose bengal in color, the new variety is the orange and yellow bicolor, with color reverse, as just described. Also, flowers of the new variety open to a flatter flower form than the blooms of "Bewitched", which tend to remain high centered.

The new variety holds its distinguishing characteristics through succeeding propagations by budding.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

THE FLOWER

The flowers are usually borne singly, on normal to strong stems of medium to long length. The quantity of bloom is abundant outdoors and it is almost continuous during the growing season. The fragrance is a tea to spicy aroma.

Bud

The peduncle is average to long in form, and of average caliper. It is erect and smooth. Its color is between Strong Yellow Green, 5GY6/8, and Moderate Yellow Green, 5GY5/6.

Before the calyx breaks, the size of the bud is medium, the length is medium, and the form is pointed and ovoid, with a conspicuous neck. There are relatively small narrow foliaceous appendages on the surface of the bud and slender foliaceous parts extending beyond the tip of the bud for a distance equal to one-quarter or more of the bud length.

As the calyx breaks, the color of the bud is between Vivid Yellow, 5Y8/12, and Vivid Yellow, 2.5Y8/12. It is lightly blushed where exposed to sunlight, with near Dark Reddish Orange, 7.5R4/11. The inner surface of the sepals has a fine tomentum, and the margins which develop on the outer surface of the bud bear several stipitate glands; other margins have a fine wooly tomentum. The outer surface is relatively smooth.

As the first petal opens, it is of average size and medium to long length. It is pointed and ovoid to urn-shaped. In color, the outside is between Moderate Orange Yellow, 10YR8/10, and Vivid Greenish Yellow, 7.5Y8/12, sometimes with near Dark Reddish Orange, 7.5R4/11, near the margins, or where the petal was exposed to the sunlight in the bud. Inside, the color is between Strong Orange, 2.5YR6/12, and Strong Reddish Orange, 7.5R5/13, with the basal area near Vivid Greenish Yellow, 7.5Y8/12. The bud opens up well and is not retarded or prevented from opening by adverse weather.

Bloom

When fully opened, the bloom is of average size, about 11 to 12 centimeters in diameter. It has double petalage, with from 25 to 35 petals plus 1 to 5 petaloids, arranged regularly. In form, the bloom is high centered at first, becoming flat to cupped, the petals remaining at first somewhat cupped but becoming later, at maturity, loosely cupped with tips reflexed slightly outward.

The petals are of medium thickness in texture. They are moderately leathery, with inside smooth and velvety, and outside slightly shiny to satiny. The shape of the outside petals is round to broadly obovate, sometimes scalloped, with one to three notches. The intermediate petals are broadly obovate. The inside petals are obovate to irregular. The colors may be modified by being striped, blotched, shaded and/or washed with other colors.

The following is a description of a newly opened flower from a rose grown outdoors in Ontario, Calif., in the month of November.

The outer surface of the outside petal is near Brilliant Yellow, 5Y9/9, at the base, blending to a mixture of hues with the overall effect of a color lighter than but near Light Orange, 5YR8/7. The inner surface of the outside petal is near Brilliant Yellow, 5Y9/9, at the base, blending through a color near Strong Orange, 5YR7/11, to a color between Light Orange, 5YR8/7, and Deep Pink, 10RP6/12.

The outer surface of the intermediate petal is near Brilliant Yellow, 5Y9/9, at the base. The remainder is between Moderate Orange Yellow, 10YR8/10, and Pale Orange Yellow, 7.5YR9/4. The inner surface of the intermediate petal is near Brilliant Yellow, 5Y9/9, blending through Moderate Orange Yellow, 10YR8/10, to a color between Light Orange, 5YR8/7, and Deep Yellowish Pink, 5R6/11.

The coloration of the inner petal is the same as that of the intermediate petal, both as to inner and outer surface.

The following description was made from a rose which had been open for three days outdoors in the month of November in Ontario, Calif.

The outer surface of the outside petal was near Brilliant Yellow, 5Y9/9, at the base, blending to near Light Yellowish Pink, 2.5YR9/3, near the margins. The inner surface of the outside petal was near Brilliant Yellow, 5Y9/9, at the base, blending through Moderate Orange Yellow, 7.5YR8/8, to near Moderate Pink, 5R8/6, near the margins.

The outer surface of the inside petal was near Brilliant Yellow, 5Y9/9, at the base, the remainder being near but lighter than Pale Orange Yellow, 7.5YR9/4. The inner surface of the inside petal was near Brilliant Yellow, 5Y9/9, at the base, with the remainder being between Moderate Orange Yellow, 7.5YR8/8, and Moderate Yellowish Pink, 10R8/6.

The general color effect of the newly opened flower is between Light Orange, 5YR8/7, and Strong Reddish Orange, 7.5R6/12. The general color effect of the bloom which has been open for three days is between Light Orange, 2.5YR8/6, and Strong Yellowish Pink, 7.5R7/9.

The petals drop off cleanly except for the petaloids, and this characteristic is not particularly affected by cold, hot, wet or dry weather.

The flowers last on the bush in the garden from 2 to 4 days in October, and cut roses grown outdoors but kept at living-room temperatures last from 2 to 3 days in October, in Southern California.

Reproductive Organs

The stamens are of average number, regularly arranged about the pistils.

The filaments are short to medium length and predominantly near Brilliant Yellow, 5Y9/9, in color. Most are with anthers.

The anthers are medium size, and all open at about the same time. Along the margins their color is near Strong Orange, 5YR7/11, just before releasing pollen. At the center portion, near attachment to the filament, the color is near Brilliant Yellow, 2.5Y9/9.

The pollen is moderate and, in color, near Strong Orange, 5YR7/11.

The pistils are few to average in number, there being approximately 90 of them.

The styles are uneven, of average length and average caliper, smooth, tightly bunched.

The stigma is near Brilliant Yellow, 2.5Y9/9.

The ovaries are usually enclosed in the calyx.

The hips are of short to average length, flat and broad. When partially mature, their color is between Strong Yellow Green, 2.5GY6/8, and Dark Greenish Yellow, 7.5Y6/7. They are smooth with thick fleshy walls.

The sepals are permanent, of medium length, spear-shaped and recurved. Their inner color is near Moderate Yellow Green, 5GY5/6, overlaid with thick grayish tomentum. The outer color is near Moderate Yellow Green, 5GY5/6.

The seeds are few to average in number, about 3 to 10, and are small to medium size.

THE PLANT

Foliage

The compound leaves usually consist of three to five leaflets. They are normal to abundant, of medium to large size, moderately heavy, smooth, leathery, and glossy. The leaflets are oval in shape, with apex acute, base obtuse, and margin simply serrate. The color of the mature leaf on its upper surface is between Moderate Olive Green, 7.5GY4/4, and Moderate Olive Green, 5GY4/3. On the under surface, the color is grayer than a color near Moderate Yellow Green, 5GY5/6.

The young leaves have an upper surface which is between Moderate Yellow Green, 5GY5/6, and Moderate Olive Green, 7.5GY4/4, sometimes lightly overlaid with near Dark Red, 5R3/7. The under surface of the young leaf is between Moderate Yellow Green, 5GY5/6, and Moderate Olive Green, 2.5GY4/3, sometimes lightly overlaid with near Dark Red, 5R3/7.

The rachis is of average size. Its upper side is grooved, with some stipitate glands on the edges. The underside is sparsely prickly, and with a few stipitate glands.

The stipules are of medium length and medium width, with medium length points turning out usually at an angle of less than 45°.

The plant possesses better than average resistance to mildew when compared to other cultivars presently in commerce which are grown under similar conditions.

Growth

In habit, the new cultivar is a bushy, upright plant much branched, of very vigorous growth. Its canes are medium caliper to heavy.

The color of the main stems is between Light Olive, 10Y5/5, and Dark Greenish Yellow, 7.5Y6/7. There are several large prickles of medium to long length which are almost straight, with medium length moderately broad bases. The color is between Moderate Brown, 7.5YR4/5, and gray. There are a few small prickles of about the same coloration as the large prickles. There are no hairs.

The color of the branches is between Strong Yellow Green, 2.5GY6/8, and Moderate Yellow Green, 2.5GY5/5. They bear several large prickles of medium to long length which are almost straight to hooked slightly downward, with medium length narrow bases. The color is between Strong Brown, 5YR4/5, and Strong Brown, 2.5YR4/7. There are a few small prickles of the same coloration as the large prickles. There are no hairs.

The color of the new shoots is near Strong Yellow Green, 2.5GY6/8, sometimes overlaid with near Dark Red, 5R3/7. The new shoots have a few large prickles which are short and hooked slightly downward, with medium length narrow bases. The color of the prickles is between Strong Yellow Green, 2.5GY6/8, and Moderate Red, 2.5R4/10. There are a few small prickles on the new shoots, but no hairs.

We claim:

1. A new and distinct variety of hybrid tea rose, substantially as described and illustrated herein, and having a tall upright bushy habit of growth, with medium size to large glossy foliage and smooth erect peduncles, the variety being characterized especially in the bicolored flowers which it bears, these comprising petals of an orange color on their inner surfaces and a yellow reverse on their outer surfaces, said flowers having from 25 to 35 petals and from 1 to 5 petaloids disposed about approximately 90 pistils.

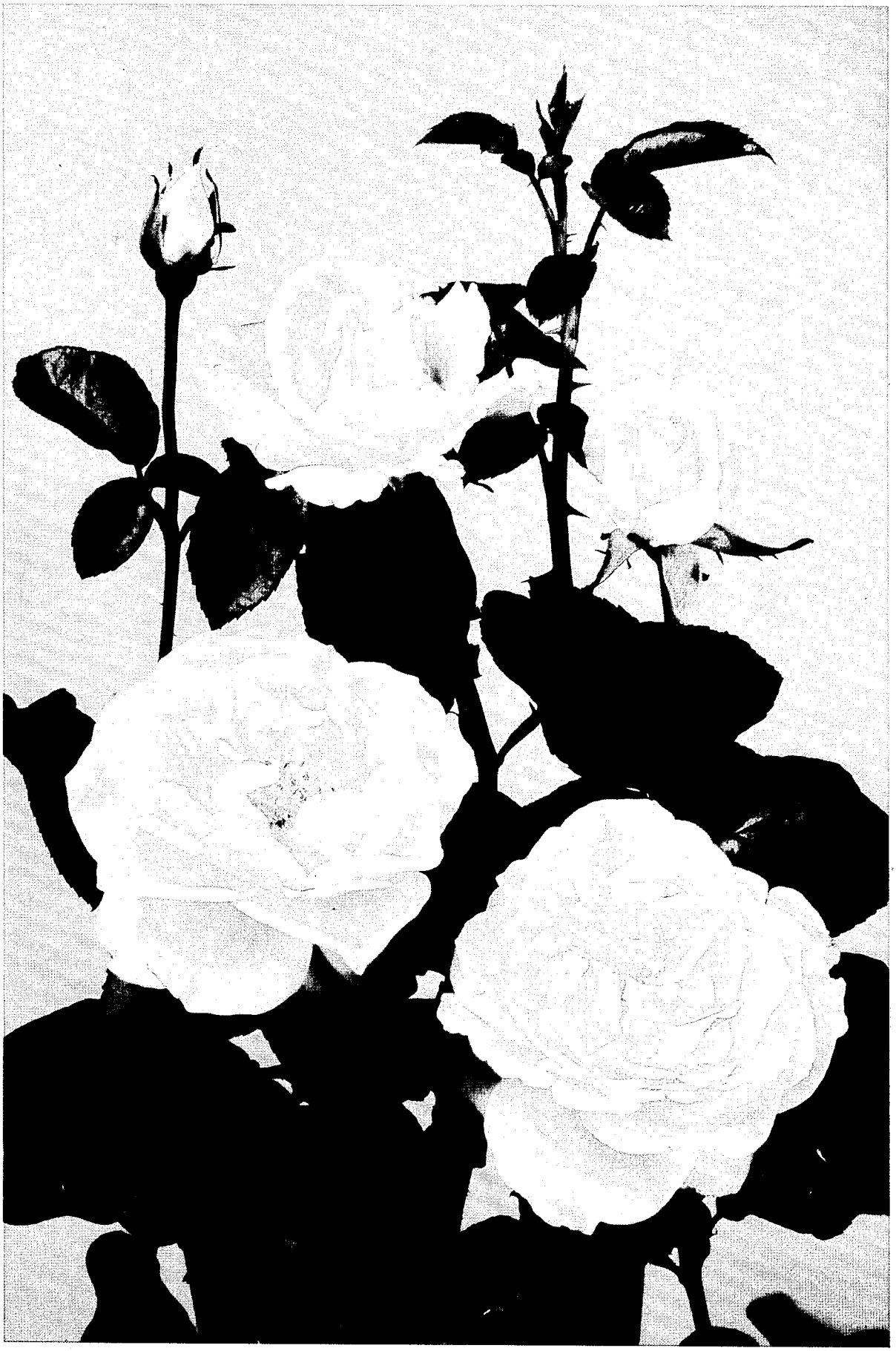

* * * * *